United States Patent
Shimizu

[11] Patent Number: 6,090,117
[45] Date of Patent: Jul. 18, 2000

[54] ARTIFICIAL NEURAL CANAL

[75] Inventor: Yasuhiko Shimizu, Uji, Japan

[73] Assignees: Yasuhiko Shimizu, Kyoto; Tapic International Co., Ltd., Tokyo, both of Japan

[21] Appl. No.: 09/308,517

[22] PCT Filed: Nov. 19, 1997

[86] PCT No.: PCT/JP97/04203

§ 371 Date: May 20, 1999

§ 102(e) Date: May 20, 1999

[87] PCT Pub. No.: WO98/22155

PCT Pub. Date: May 28, 1998

[30] Foreign Application Priority Data

Nov. 20, 1996 [JP] Japan .................................. 8-308854

[51] Int. Cl.[7] ...................................................... A61B 17/08
[52] U.S. Cl. .............................................. 606/152; 623/12
[58] Field of Search ....................................... 606/152, 153, 606/154, 155; 623/12, 16, 66; 514/21

[56] References Cited

U.S. PATENT DOCUMENTS

| 5,147,399 | 9/1992 | Dellon et al. | 623/12 |
| 5,656,605 | 8/1997 | Hansson et al. | 514/21 |

*Primary Examiner*—Michael Buiz
*Assistant Examiner*—Lien Ngo
*Attorney, Agent, or Firm*—David G. Conlin; Robert L. Buchanan; Dike, Bronstein, Roberts & Cushman, LLP

[57] ABSTRACT

The present invention offers an artificial tube for nerve which can remain in the body until the nerve regenerates while does not remain as a foreign body in the body following nerve regeneration, and which induces axons regenerated from severed nerve stumps, can promote infiltration of blood capillaries from the body and regeneration of nerve tissue. The present invention comprises a tube 10 or 20 having coating layers 12, 13 or 22, 23 composed of gelatin or collagen on the inner and outer surfaces of a tube 11 or 21 composed of a material being biodegradable and absorbable in vivo, and a collagen body 30 or 40 having cavities 32, 33 or 41 which pass through said tube so as to be substantially parallel to the axis of said tube; wherein, said cavities are filled with a matrix gel.

9 Claims, 1 Drawing Sheet

ARTIFICIAL NEURAL CANAL

TECHNICAL FIELD

The present invention relates to an artificial tube for nerve.

BACKGROUND ART

In the case of peripheral nerve is severed surgically or severed due to injury, an initial attempt is made to directly anastomose the stumps of the severed peripheral nerve. In many cases, however, it is impossible to accurately anastomose the severed nerve directly resulting in the nerve being left in the severed state. Consequently, although the nerve attempts to regenerate towards the distal side, it is impaired by connective tissue. Hence, regeneration stops with the formation of a neuroma at the severed end without reaching the neural stump on the distal side. As a result, the function of the severed nerve is frequently not restored after the surgical wound or injury has healed, and sequella remain. In cases in which direct anastomosis is impossible, a peripheral nerve having a function which is not very important may be partially excised from the same patient, and autotransplantation may be performed to the severed site of the nerve using this peripheral nerve segment. However, in this method as well, not only are there many cases in which nerve function is not adequately restored, but there are also many cases in which decreased function is observed even at the portion at which the transplanted nerve is used.

Therefore, numerous attempts have been made to restore function by connecting the stumps of severed peripheral nerves with a tube-shaped medical material, namely an artificial tube for nerve, regenerating the axon from the stump on the central side of the nerve trunk towards the stump on the distal side, inducing the nerve to extend in the proper direction, and allowing the nerve to reach a myoneural junction or peripheral sensory receptor from the peripheral nerve trunk. In the past, non-porous tubes made of silicone, polyethylene or polyvinyl chloride, porous tubes made of drawn polytetrafluoroethylene or cellulose, semipermeable membrane tubes made of polyacrylonitrile or polysulfone, tubes made of biodegradable materials such as polyglycolic acid, polylactic acid or their copolymers, gelatin tubes, or biological tissue tubes originating in the same species such as arteries and veins. However, in regeneration experiments on peripheral nerves using these materials, since biological repair is impaired by the material, the length of nerve that has been able to be regenerated thus far has been at most on the order of 15 mm. In addition, not only is the regenerated nerve narrow without the form of the nerve being normally restored, but there are many cases in which the function of the regenerated nerve is not restored. In addition, although examples have been reported in which neural growth factor NGF is filled into a tube, since NGF ends up rapidly running out of the tube and dispersing, remarkable effects have not been obtained.

Although artificial tubes for nerve which comprise collagen tubes in which collagen fibers on which laminin and fibronectin are coated are filled (Tong, X., et al., Brain Research 663: 155–162 (1994)) have recently been attempted, since the collagen tubes are unable to remain without being broken down until the nerve is regenerated to an adequate length, satisfactory results have not been obtained.

On the other hand, the spinal cord is considered to not regenerate once it has been damaged. In the case the spinal cord is damaged due to injury or tumor, the damaged spinal cord does not regenerate, and all function below the damaged portion is lost with paralysis remaining as the sequella. Recently however, experiments on animals have begun to be conducted that prove that the spinal cord is also able to regenerate. In the case the spinal cord is severed sharply and accurately re-sutured, function is restored and the damaged portion is repaired to a considerable degree. In addition, if a portion of the spinal cord is excised in the form of a tube and an intercostal nerve fasicle is implanted at that site, the portion of the spinal cord regenerates and function is at least partially restored. If a portion of the spinal cord is excised in the form of a tube, and fetal spinal cord is transplanted to that site, spinal cord function and form are restored. These findings have been observed in experiments in rats. In this case as well, it is recognized that regeneration occurs only in the case the transplanted fetal spinal cord segment is transplanted by properly aligning the respective neural processes. Based on the above findings, although it has been determined that regeneration of the spinal cord can occur by inducing the spinal cord so as to properly align the compartments of regenerated tissue, there have been no artificial tubes for spinal cord developed whatsoever that actually allow spinal cord regeneration.

Therefore, in order to control the rate of decomposition in the body so as to remain in the body until the nerve regenerates while also allowing degradation and absorption in the body as nerve regeneration progresses, the development of an artificial tube for nerve is desired that induces axons regenerated from severed nerve stumps to extend in the proper direction without pressing on the regenerated nerve following nerve regeneration, and causes rapid restoration of blood flow by promoting infiltration of blood capillaries from the body to promote regeneration of nerve tissue. In addition, there is also an urgent need for the development of an artificial tube for spinal cord that connects not only peripheral nerves but also the missing portions of spinal cord, and promotes proper regeneration of spinal cord tissue along with restoration of function.

DISCLOSURE OF INVENTION

The present invention relates to an artificial tube for nerve which comprises a tube 10 or 20 having coating layers 12, 13 or 22, 23 composed of gelatin or collagen on the inner and outer surfaces of a tube 11 or 21 composed of a material being biodegradable and absorbable in vivo, and a collagen body 30 or 40 having cavities 32, 33 or 41 which pass through said tube so as to be substantially parallel to the axis of said tube; wherein, said cavities are filled with a matrix gel containing collagen, laminin, heparan sulfate proteoglycans, entactin and growth factor. The present invention also relates to a method for producing the above-mentioned artificial tube for nerve including following steps: preparing a tube 10 or 20 having coating layers 12, 13 or 22, 23 composed of gelatin or collagen on the inner and outer surfaces of a tube 11 or 21 composed of a material being biodegradable and absorbable in vivo; inserting a collagen fiber bundle so as to be substantially parallel to the axis of said tubes; subjecting to crosslinking treatment; and filling a matrix gel containing collagen, laminin, heparan sulfate proteoglycans, entactin and growth factor into cavities 32 between said collagen fibers 31 within said tube and into cavities 33 between said collagen fibers and said tube. Moreover, the present invention also relates to a method for producing the above-mentioned artificial tube for nerve including following steps: preparing a tube 10 or 20 having coating layers 12, 13 or 22, 23 composed of gelatin or collagen on the inner and outer surfaces of a tube 11 or 21 composed of a material being biodegradable and absorbablein vivo; inserting rod-shaped cores so as to be substantially parallel to the axis of said tube; filling said tube with a collagen solution; subjecting to crosslinking treatment; removing the cores; obtaining a tube having in its lumen a collagen gel in which cavities 41 are formed in the form of holes that pass through said tube; and filling said cavities with a matrix gel containing collagen, laminin, heparan sulfate proteoglycans, entactin and growth factor.

The artificial tube for nerve of the present invention which comprises a tube 10 or 20 having coating layers 12, 13 or 22, 23 composed of gelatin or collagen on the inner and outer surfaces of the tube 11 or 21 composed of a material being biodegradable and absorbable in vivo, and a collagen body 30 or 40 having cavities 32, 33 or 41 that pass through said tube so as to be substantially parallel to the axis of said tube, wherein, said cavities are filled with a matrix gel containing collagen, laminin, heparan sulfate proteoglycans, entactin and growth factor. Although the length and inner diameter of the tube that compose the artificial tube for nerve of the present invention differs according to the length of the severed portion of the nerve and the thickness of the nerve, in order to cover, for example, a missing portion on the order of about 25 mm of the sciatic nerve of a cat, the length is about 28–35 mm, and preferably about 30 mm, and the inner diameter is about 1–8 mm, and preferably about 4 mm. In addition, in the case of using the artificial tube for nerve of the present invention as an artificial tube for spinal cord as well, the length of the tube is determined according to the length of the severed portion, while the inner diameter is preferably about 2–12 mm, and particularly preferably about 10 mm.

It is necessary that the tube composed of a material being biodegradable and absorbable in vivo that composes the artificial tube for nerve of the present invention retains the shape of the tube to prevent invasion of body cells from outside the tube during the time until the severed nerve regenerates and the severed location is rejoined (about 1–3 months). Consequently, a tube comprising a mesh material made of a material selected from the group consisting of polyglycolic acid, polylactic acid (L or DL), copolymer of glycolic acid and lactic acid, copolymer of lactic acid and e-caprolactone, polydioxanone and copolymer of glycolic acid and trimethylene carbonate, which is able to maintain its shape in the body for a certain period of time despite being biodegradable and absorbable in vivo, is preferable, and a tube comprising a mesh material made of polyglycolic acid is particularly preferable. In addition, a tube comprising a material made of fine fibrous collagen can also be preferably used in addition to the tube comprising the mesh material made of the material being biodegradable and absorbable in vivo such as polyglycolic acid.

To begin with, a description is provided of the artificial tube for nerve of the present invention having coating layers 12 and 13 composed of gelatin or collagen on the inner and outer surfaces of a tube 11 comprising a mesh material made of a material being biodegradable and absorbable in vivo such as polyglycolic acid. Although tube 11 comprising a mesh material made of polyglycolic acid has an inner diameter and length as described above, in order to allow it to retain the tubular shape of the artificial tube for nerve for about 1–3 months, the membrane thickness of said tube is preferably about 0.1–3 mm, and particularly preferably about 0.5–2 mm. If the membrane thickness exceeds 3 mm, the tube obstructs regeneration of body tissue, and if the membrane thickness is less than 0.1 mm, degradation and absorption of the tube proceeds too rapidly, and the shape of the tube is not maintained until the nerve finishes regenerating. In addition, in the case of using the artificial tube for nerve of the present invention as an artificial tube for spinal cord, its membrane thickness should preferably be about 0.2–5 mm, and particularly preferably about 0.5–3 mm.

In the case the material being biodegradable and absorbable in vivo is a material such as polyglycolic acid, the tube 11 is in the form of a mesh to ensure water permeability for hydrophobic tube 11. The mesh pore size of this mesh tube 11 is preferably about 10–300 $\mu$m, and particularly preferably about 100–200 $\mu$m. If the mesh pore size is less than 10 $\mu$m, cells and tissue are unable to proliferate, while if the mesh pore size exceeds 300 $\mu$m, entry of tissue becomes excessive.

In the case of the tube 11 comprising a mesh material made of a material such as polyglycolic acid, although it has coating layers 12 and 13 composed of gelatin or collagen, which are materials having tissue regeneration promoting action, on its inner and outer surfaces since it itself has no action that promotes tissue regeneration, it is particularly preferable that the inside surfaces of the mesh pores also be coated in addition to the inner and outer surfaces of tube 11. The thickness of the coating layers 12 and 13 is preferably about 0.2–5 mm, and particularly preferably about 0.5–3 mm in the case of the collagen coating layer, and preferably about 0.2–5 mm, and particularly preferably about 0.5–3 mm in the case of the gelatin coating layer. Examples of such materials that promote tissue regeneration include collagen and gelatin which have water-permeability, do not cause foreign body reactions when applied in the body, have excellent bioaffinity and tissue compatibility, and have an action that promotes tissue regeneration. Collagen originating in various animals conventionally used in the past can be used for the collagen raw material, preferable examples of which include type I collagen or a mixed collagen of type I and type III collagen originating in the skin, bone, cartilage, tendon and organs of cows, pigs, rabbits, sheep, kangaroos or birds that is solubilized by acid, base, enzymes and so forth. The coating layers composed of collagen are layers having an amorphous structure in which collagen molecules are dispersed. Purified gelatin according to Japanese Pharmacopoeia can be used for the raw material of the coating layer composed of gelatin.

In the artificial tube for nerve of the present invention, the tube 11 or 21 composed of a material being biodegradable and absorbable in vivo can be the tube 11 composed of a mesh material made of a material such as the abovementioned polyglycolic acid, or the tube 21 composed of a material made of fine fibrous collagen that uses collagen having tissue regeneration promoting action for its raw material. The following provides a description of the artificial tube for nerve of the present invention in which the material being biodegradable and absorbablein vivo is a material composed of fine fibrous collagen, and coating layers 22, 23 of tube 21 are composed of collagen.

Type I collagen or a mixed collagen of type I and type III of animal origin like that described above that has been used in the past and is solubilized by acid, base or enzymes and so forth is preferable for the collagen used for the raw material of the material being biodegradable and absorbable in vivo. This material composed of fine fibrous collagen is a non-woven fabric-like substance in which fine fibers composed of collagen molecules are overlapped in multiple layers, and tube 21 which uses this as its material has an inner diameter and length like those described above. The membrane thickness is preferably about 0.5–5 mm, and particularly preferably about 1–2 mm. In addition, in the case of using the artificial tube for nerve of the present invention as an artificial tube for spinal cord, the membrane thickness is preferably about 0.5–5 mm, and particularly preferably about 1–3 mm. In addition, coating layers 22, 23 composed of collagen formed on the inner and outer surfaces of this tube 21 use conventional solubilized type I collagen or a mixed collagen of type I and type III of animal origin as previously described,, for their raw material, and have an amorphous structure in which collagen molecules are dispersed. The thickness of the coating layers is preferably about 0.1–2 mm, and particularly preferably about 0.5–1 mm.

The artificial tube for nerve of the present invention comprises a tube 10 or 20 having coating layers 12, 13 or 22, 23 composed of gelatin or collagen on the inner and outer layers of a tube 11 or 21 composed of a material being biodegradable and absorbable in vivo as was previously described in detail, and a collagen body 30 or 40 having cavities 32, 33 or 41 in its lumen that pass through the tube 10 or 20 substantially parallel to the axis of the tube 10 or 20. Moreover, said cavities are filled with a matrix gel containing collagen, laminin, heparan sulfate proteoglycans, entactin and growth factor. When this artificial tube for nerve is applied in the body, the surfaces of the cavities in the collagen body of the tube lumen are used as footholds for regeneration by nerve fibers, and nerve fibers regenerate and extend into those cavities.

As a preferable mode of the present invention, the tube 10 or 20 composed of a material being biodegradable and absorbable in vivo is subjected to crosslinking treatment, and the collagen body 30 within its lumen is a crosslinked collagen fiber bundle inserted so as to be substantially parallel to the axis of said tube. Moreover, cavities 32 between collagen fibers 31 and cavities 33 between collagen fibers 31 and the tube 10 or 20 are either filled with the above-mentioned matrix gel, or collagen body 40 within its lumen is a crosslinked collagen gel having cavities 41 in the form of holes that pass through said tube substantially parallel to the axis of said tube, and said cavities are filled with the above-mentioned matrix gel.

It is preferable that the collagen fiber bundle be type I collagen fibers obtained by solubilizing collagen originating in the skin or bone and so forth of various animals as used in the past with acid, base or enzyme, and its diameter is preferably about 10–30 $\mu$m, and particularly preferably 20 $\mu$m. In the case of using the artificial tube for nerve of the present invention as an artificial tube for spinal cord, the diameter of fibers 31 is preferably about 10–30 $\mu$m, and particularly preferably about 20 $\mu$m. The percentage of void of tubes 10, 20 is preferably about 70–98%, and particularly preferably about 90–95%. In the case of an artificial tube for spinal cord, percentage of void is preferably about 70–98%, and particularly preferably about 90–95%. For example, in the case of a tube having an inner diameter of 4 mm, about 2000 collagen fibers 31 having a diameter of about 20 $\mu$m are filled. In addition, it is preferable that these collagen fibers 31 be coated in advance with the above-mentioned matrix gel (not shown).

In addition, cavities 41 in the form of holes that pass through the tube so as to be substantially parallel to the axis of the tube must have a pore size that is necessary for regenerated nerve fibers to extend inside following application of the artificial tube for nerve of the present invention in the body, and that pore size is preferably about 30–200 $\mu$m, and particularly preferably about 80 $\mu$m. In addition, although the number of cavities varies according to the thickness of the artificial tube for nerve, in the case of, for example, a tube having an inner diameter of 4 mm, the number of cavities is preferably about 5–20, and particularly preferably about 12. In the case of using the artificial tube for nerve of the present invention as an artificial tube for spinal cord, the pore size of cavities 41 that pass through a tube is preferably about 30–200 $\mu$m, and particularly preferably about 80 $\mu$m, and the number of cavities is preferably about 20–150, and particularly preferably about 50, in the case of, for example, a tube having an inner diameter of 10 mm. In addition, crosslinked collagen gel having cavities 41 in the form of holes that pass through a tube is gelled by performing crosslinking treatment on type I collagen obtained by solubilizing collagen originating in the skin, bone and so forth of various animals as used in the past with acid, base or enzyme.

The following provides a description of the method for producing the artificial tube for nerve of the present invention. In order to produce the artificial tube for nerve of the present invention in which the material being biodegradable and absorbable in vivo is a mesh material composed of a material selected from the group consisting of polyglycolic acid, polylactic acid, copolymer of glycolic acid and lactic acid, copolymer of lactic acid and ε-caprolactone, polydioxanone and copolymer of glycolic acid and trimethylene carbonate, and having coating layers 12, 13 composed of gelatin or collagen on the inner and outer surfaces of tube 11, tube 11 composed of a mesh material using polyglycolic acid and so forth for the material is first prepared. Although the tube 11 may be prepared by any method, a mesh tube having the above-mentioned layers is obtained by, for example, weaving fibers of polyglycolic acid and so forth (having a diameter of, for example, 0.1 mm) into the shape of a cylinder. The prepared tube 11 composed of the mesh material is immersed in a solution of the above-mentioned collagen or gelatin and dried to form collagen or gelatin coating layers 12, 13 on the outer and inner surfaces of tube 11 as well as on the inner surfaces of the mesh pores. In order to coat tube 11 with collagen or gelatin, an approximately 1 N hydrochloric acid solution (pH of about 3) preferably containing about 1–3 wt %, and particularly preferably about 1–2 wt %, of collagen, or preferably an about 2–30 wt %, and particularly preferably about 10–20 wt %, aqueous gelatin solution is used. In addition, it is convenient to coat the collagen or gelatin on the surface of tube 11 composed of a mesh material composed of polyglycolic acid and so forth after treating with plasma discharge, ozone irradiation and so forth.

In order to prepare the artificial tube for nerve of the present invention in which the material being biodegradable and absorbable in vivo is a material composed of fine fibrous collagen, coating layers 22 and 23 of tube 21 are composed of collagen, and, for example, a rod made of Teflon and so forth having a diameter of about 1–8 mm, and preferably about 4 mm, is used for the core. In the case of using the artificial tube for nerve of the present invention as an artificial tube for spinal cord, the rod having a diameter of preferably about 2–12 mm, and particularly preferably about 10 mm, is used. The core are immersed in an approximately 1 N hydrochloric acid solution containing preferably about 0.5–3 wt %, and particularly preferably about 1–2 wt %, of collagen, and a collagen hydrochloric acid solution layer having a thickness of preferably about 5–20 mm, and particularly preferably about 10 mm, is formed on the surface of said core followed by freezing (for example, at about 0° C. for about 12 hours). In the case of using the artificial tube for nervus of the present invention as an artificial tube for spinal cord, a collagen hydrochloric acid solution layer is formed having a thickness of preferably about 5–30 mm, and particularly preferably about 20 mm, followed by freezing. As a result of freezing, fine fragments of ice form between the collagen molecules dispersed in the hydrochloric acid solution, layer separation occurs in the collagen hydrochloric acid solution, and fine fibers are formed due to rearrangement of the collagen molecules. Next, this is further freeze-dried (for example, at about 0° C. for about 24 hours) in a vacuum. As a result of freeze-drying, in addition to the fine ice fragments between the collagen molecules vaporizing, a tube is obtained composed of a nonwoven fabric-like collagen layer in which fine fibers overlap in multiple layers.

Next, the core on which is formed this fine fibrous collagen layer is placed in a pouch made of polyethylene and so forth, sealed and degassed followed by compression of the collagen layer. As a result of compressing, high-density, fine fibrous collagen layer 21 is obtained. Alternatively, the collagen layer may be compressed by pressing without degassing. Compression is performed such that the thickness of the collagen layer after compression is preferably about 0.5–5 mm, and particularly preferably about 1–2 mm. In the case of using as an artificial tube for spinal cord, compression is performed such that the thickness of the collagen layer is preferably about 0.5–5 mm, and particularly preferably about 1–3 mm.

Collagen membranes 22 and 23 are additionally formed on the inner and outer surfaces of the compressed, fine fibrous collagen layer 21. As a result of forming these collagen membranes 22 and 23, an artificial tube for nerve is obtained having even greater strength. In order to form these collagen membranes 22 and 23, the tube composed of fine fibrous collagen layer 21 removed from the above-mentioned rod is again immersed in an approximately 1 N hydrochloric acid solution containing preferably about 0.5–3 wt %, and particularly preferably about 1–2 wt %, collagen, and respectively forming collagen hydrochloric acid solution layers on the inner and outer surfaces of fine fibrous collagen layer 21 followed by air drying. This immersion and air drying procedure is repeated several times, and preferably 20 times, to obtain collagen membranes 22, 23 having an amorphous structure in which collagen molecules are dispersed (the thicknesses of the collagen hydrochloric acid solution layers are each preferably about 0.2–1.0 mm, and particularly preferably about 0.5 mm). In the case of using the artificial tube for nerve of the present invention as an artificial tube for spinal cord, the thicknesses of collagen membranes 22, 23 formed on the inner and outer surfaces of fine fibrous collagen layer 21 are preferably about 0.2–1.0 mm, and particularly preferably about 0.5 mm.

Tube 20 prepared in this manner can be handled easily and allows easy suturing with nerves due to its high tear strength as compared with a tube consisting of collagen membrane alone.

A collagen body 30 or 40 having cavities 32, 33 or 41 that pass through the tube so as to be substantially parallel to the axis of the tube is formed in the lumen of the tube 10 or 20 in which coating layers 12, 13 or 22, 23 composed of collagen or gelatin are formed on the inner and outer surfaces of the tube 11 or 21 composed of a material being biodegradable and absorbable in vivo prepared in the manner described above. This collagen body 30 or 40 serves as a foothold during nerve fiber regeneration and extension, and nerve fibers regenerate and extend into cavities 32, 33 or 41 within its collagen body 30 or 40.

More specifically, type I collagen fiber bundle is inserted into the tube 11 or 21 prepared in the manner described above so as to be substantially parallel to the tube axis. As a result of inserting the collagen fiber bundle, nerve cells are allowed to grow in cavities 32 between each collagen fiber 31 that composes the fiber bundle, and in cavities 33 between collagen fibers 31 and tube 10 or 20. Type I collagen fibers obtained by solubilizing collagen originating in the skin, bone and so forth of various animals used conventionally with acid, base or enzyme can be used for the collagen serving as the raw material of the collagen fiber bundles used here. The diameter of the collagen fibers used here is preferably about 10–30 $\mu$m, and particularly preferably about 20 $\mu$m, and collagen fibers are inserted so as to reach the above-mentioned percentage of void.

Next, crosslinking treatment is preferably performed on tubes 10, 20 composed of a material being biodegradable and absorbable in vivo prepared in the manner described above. Crosslinking treatment is advantageous for the artificial tube for nerve of the present invention because it maintains the shape of the tube and prevents invasion of cells from outside the artificial tube for nerve during the time until the peripheral nerve is finished regenerating.

Although varying according to the length of the severed nerve portion that requires regeneration, crosslinking treatment is performed for 1–3 months after application in the body to an extent that the shape of the tube is retained. Although examples of crosslinking methods include gamma ray crosslinking, ultraviolet ray crosslinking, electron beam crosslinking, thermal dehydration crosslinking, glutaraldehyde crosslinking, epoxy crosslinking and water-soluble carbodiimide crosslinking, thermal dehydration crosslinking is preferable because it is easy to control the degree of crosslinking and does not have an effect on the body even when used for crosslinking treatment. Crosslinking treatment is performed in a vacuum at a temperature of, for example, about 105–150° C., preferably about 120–150° C., and particularly preferably about 140° C. for, for example, about 6–24 hours, preferably about 6–12 hours and particularly preferably about 12 hours.

Next, a matrix gel containing components that promote nerve fiber growth is filled into cavities 32 between collagen fibers 31 of tube 10 or 20 composed of a material being biodegradable and absorbable in vivo on which crosslinking treatment has been performed, and into cavities 33 between collagen fibers 31 and tube 10 or 20, to obtain the artificial tube for nerve of the present invention. The matrix gel contains extracted collagen (and particularly type IV collagen at, for example, 30%), laminin (for example, 50–60%), heparan sulfate proteoglycans (for example, 2–5%), entactin (for example, 5–10%) as well as growth factor such as EGF (epidermal growth factor), $\beta$FGF (fibroblast growth factor), NGF (nerve growth factor), PDGF (platelet-derived growth factor), IGF-1 (insulin-like growth factor) and TGF-B (transforming growth factor), which promote fiber regeneration.

As described above, the fibers of the collagen fiber bundle inserted into tube 10 or 20 composed of a material being biodegradable and absorbable in vivo prior to crosslinking treatment are respectively coated in advance with matrix gel containing components that promote nerve fiber growth. It is preferable that this matrix gel contains the same components as the above-mentioned matrix gel. Methods such as immersion or coating may be used to coat the collagen fibers with matrix gel.

More specifically, rod-shaped cores composed of a material having elasticity may alternatively be inserted into tube 10 or 20 prepared in the above manner so as to be substantially parallel to the axis of the tubes, and the tube into which the rod-shaped cores are inserted is immersed in a type I collagen solution or a type I collagen solution may be injected into it, followed by subjecting to crosslinking treatment and then removing the cores to obtain a tube having collagen gel in its lumen that forms cavities 41 in the form of holes that pass through the tube. Nerve fibers regenerate and extend into these holes 41 formed in the above described manner after applying the artificial tube for nerve of the present invention in the body. Thus, it is necessary that the rod-shaped cores used to form holes 41 that pass through the tube have a pore size that allows extension of regenerating nerve fibers, and that pore size is preferably about 30–200 μm, and particularly preferably about 80 μm. In addition, although varying according to the thickness of the artificial tube for nerve, the number of cores that are inserted into the tube is preferably 5–20, and particularly preferably about 12 in the case of a tube having an inner diameter of, for example, 4 mm. In the case of using the artificial tube for nerve of the present invention as an artificial tube for spinal cord, the number of cores inserted into the tube is preferably about 20–150, and particularly preferably about 50, in the case of a tube having an inner diameter of, for example, 10 mm. In addition, the type I collagen solution that is filled is prepared by dissolving type I collagen, obtained by solubilizing conventionally used collagen originating in the skin, bone and so forth of various animals with acid, base or enzyme, in approximately 1 N hydrochloric acid, and preferably contains about 0.5–3 wt %, and particularly preferably about 1 wt %, of type I collagen.

Crosslinking treatment is performed in the same manner as described above by performing thermal crosslinking in a vacuum at a temperature of, for example, about 105–150° C., preferably about 120–150° C., and particularly preferably about 140° C., for, for example, about 6–24 hours, preferably about 6–12 hours, and particularly preferably about 12 hours. If the crosslinking temperature exceeds 150° C., the strength of the material being biodegradable and absorbable in vivo decreases, and if the temperature is below 105° C., the crosslinking reaction does not take place adequately.

Moreover, a matrix gel having the same components as described above is filled into cavities 41 in the form of holes that pass through the tubes formed as described above by impregnation or other routine method followed by aspiration as necessary to obtain the artificial tube for nerve of the present invention.

The artificial tube for nerve prepared in the manner described above can be used to restore nerve function by inserting both stumps of a nerve that has been severed by injury or surgical procedure into the present artificial tube for nerve and ligating those portions to induce axon regeneration and extension in the proper direction, and allow axons to reach from the peripheral nerve trunk to a neuromuscular junction or peripheral sensory receptor. In addition, in the case the spinal cord is damaged due to injury as well, by removing the vertebrae corresponding to the damaged portion and covering the damaged portion of the spinal cord with the present artificial tube for nerve, it is believed that the damaged spinal cord can be regenerated and its function restored.

BEST MODE FOR CARRYING OUT THE INVENTION

Figure 1:
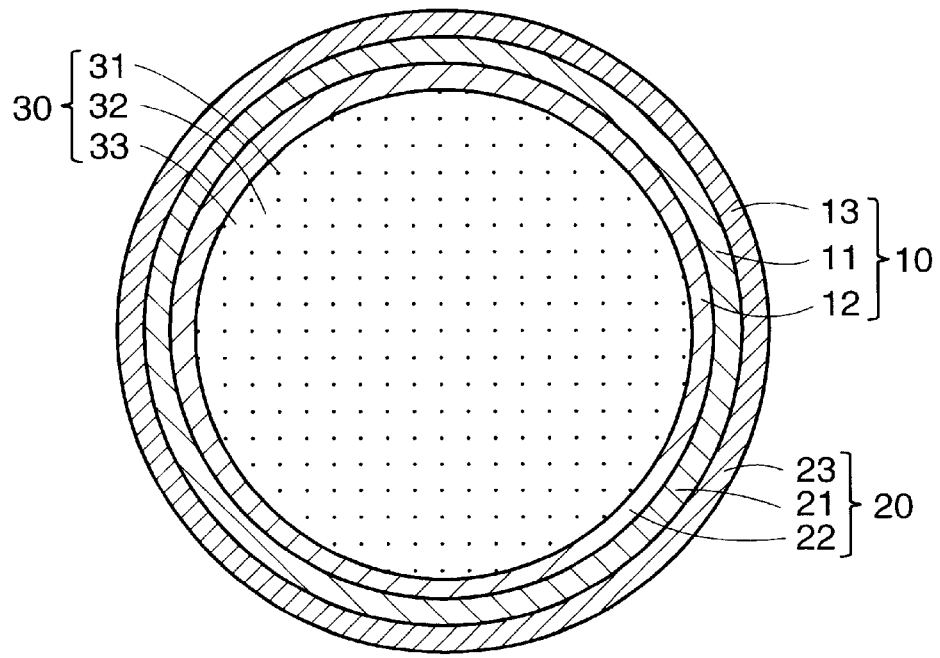
FIG. 1 is a drawing showing a cross-section of one example of an artificial tube for nerve as claimed in the present invention.
Figure 2:
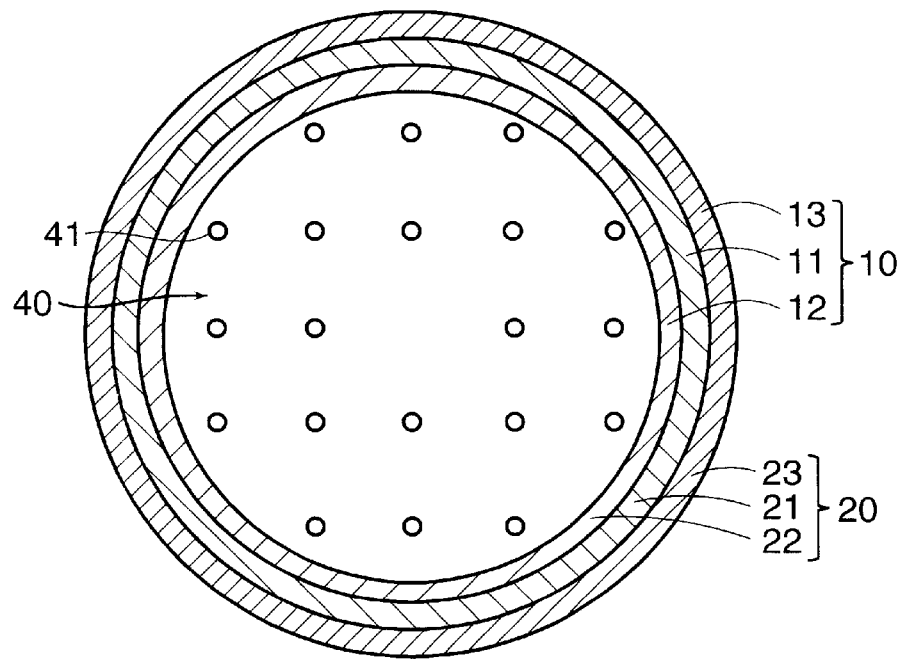
FIG. 2 is a drawing showing a cross-section of another example of an artificial tube for nerve as claimed in the present invention (the constitutions of these examples are illustrated schematically, and dimensions shown are not actual dimensions).

Although the following provides a detailed explanation of the present invention through its examples and comparative examples, the present invention is not limited to these.

EXAMPLE 1

Polyglycolic acid (PGA) fibers (diameter: 0.1 mm) were woven into a tubular shape to prepare a polyglycolic acid mesh tube (mesh pore size: approximately 100–200 μm) having a length of about 30 mm, inner diameter of about 4–5 mm, and membrane thickness of about 1 mm. By immersing this mesh tube in 1 N hydrochloric acid solution containing 1.0 wt % enzyme-solubilized collagen originating in pig skin and then drying, the outer and inner surfaces of the tube along with the inside surfaces of its mesh pores were coated with said collagen.

1 g of type IV collagen, 2 g of laminin, 0.2 g of heparan sodium proteoglycans, 0.4 g of entactin, 2 ng of EGF, 0.5 ng of β-FGF, 1 ng of NGF, 3 pg of PDGF, 2 ng of IGF-1 and 1 ng of TGF-β were dissolved in 2 ml of physiological saline to prepare a matrix gel containing the above-mentioned components. Enzyme-solubilized collagen fibers originating in pig skin (diameter: 0.20 μm) were then immersed in this matrix gel to coat the surfaces of each fiber, after which 2000 of these coated fibers were inserted into the tube having the collagen coating layer obtained in the manner described above. Moreover, the tube was subjected to thermal dehydration crosslinking treatment in a vacuum at 150° C. for 24 hours. Finally, the matrix gel was filled between the tube and collagen fibers to obtain the artificial tube for nerve of the present invention.

25 mm of the sciatic nerve of a cat (body weight: 5 kg) was excised, the nerve stumps on both sides were inserted into the above-mentioned artificial tube for nerve and connected by ligating with 10-0 Nylon thread.

Axon transport was observed by HRP staining, and physiological function was observed by cerebrosomatic sensory induction potential and induction electromyograms immediately after or 1, 2, 3 or 4 months after surgery. The cat was sacrificed and the form of the sciatic nerve was observed both macroscopically and optical-microscopically.

Recovery of both the form and function of the sciatic nerve was already observed one month after surgery, and the state of the regenerated nerve approached that of the normal state.

COMPARATIVE EXAMPLE 1

With the exception of not inserting the collagen fiber bundle into the lumen, the mesh tube composed of polyglycolic acid having the collagen coating layers was prepared using the method described in Example 1, the mesh tube was subjected to thermal dehydration crosslinking treatment, and filled with the matrix gel.

25 mm of the sciatic nerve of a cat (body weight: 5 kg) was excised, the nerve stumps on both sides were inserted into the tube prepared in the above manner and connected by ligating with 10-0 Nylon thread.

Axon transport was observed by HRP staining, and physiological function was observed by cerebrosomatic sensory induction potential and induction electromyograms immediately after or 1, 2, 3 or 4 months after surgery. The cat was sacrificed and the form of the sciatic nerve was observed both macroscopically and optical-microscopically. As a result, recovery of form and function of the sciatic nerve was observed two months after surgery.

EXAMPLE 2

As a result of immersing Teflon rod having a length of about 10 cm and diameter of about 4–5 mm in a 1 N hydrochloric acid solution containing about 1 wt % of enzyme-solubilized collagen originating in pig skin and then taking them out of the above-mentioned solution, a collagen hydrochloric acid solution layer having a thickness of about 10 mm was formed on the surface of the Teflon rod, after which it was frozen at about 0° C. for about 12 hours. The rod was then freeze-dried at about 0° C. for about 24 hours in a vacuum to transform the collagen hydrochloric acid solution layer into a fine fibrous collagen layer. The Teflon rod having a fine fibrous collagen layer formed on the surface was then compressed with a press to compress the fine fibrous collagen layer to a thickness of about 1 mm. Next, the compressed fine fibrous collagen layer was removed from the Teflon rod, and the tube composed of this fine fibrous collagen layer was again immersed in the previous approximately 1 wt % collagen hydrochloric acid solution. By thus forming a collagen hydrochloric acid layer on the inner and outer surfaces of the fine fibrous collagen layer and air drying (this procedure of immersing in collagen hydrochloric acid solution followed by air drying was repeated 20 times), collagen membranes were formed on the inner and outer surfaces of the fine fibrous collagen layer. In this manner, a tube composed of fine fibrous collagen was prepared having coating layers composed of collagen on its outer and inner surfaces.

1 g of type IV collagen, 2 g of laminin, 0.2 g of heparan sodium proteoglycans, 0.4 g of entactin, 2 ng of EGF, 0.5 ng of β-FGF, 1 ng of NGF, 3 pg of PDGF, 2 ng of IGF-1 and 1 ng of TGF-β were dissolved in 2 ml of physiological saline to prepare a matrix gel containing the above-mentioned components. Enzyme-solubilized collagen fibers originating in pig skin (diameter: 0.20 μm) were then immersed in this matrix gel to coat the surfaces of each fiber, after which 2000 of these coated fibers were inserted into the tube having the collagen coating layers obtained in the manner described above. Moreover, the tube was subjected to thermal dehydration crosslinking treatment in a vacuum at 150° C. for 24 hours. Finally, the above-mentioned matrix gel was filled between the tube and collagen fibers to obtain the artificial tube for nerve of the present invention.

25 mm of the sciatic nerve of a cat (body weight: 5 kg) was excised, the nerve stumps on both sides were inserted into the above-mentioned artificial tube for nerve and connected by ligating with 10-0 Nylon thread.

Axon transport was observed by HRP staining, and physiological function was observed by cerebrosomatic sensory induction potential and induction electromyograms immediately after or 1, 2, 3 or 4 months after surgery. The cat was sacrificed and the form of the sciatic nerve was observed both macroscopically and optical-microscopically.

Recovery of both the form and function of the sciatic nerve was already observed one month after surgery, and the state of the regenerated nerve approached that of the normal state.

COMPARATIVE EXAMPLE 2

With the exception of not inserting the collagen fiber bundle into the lumen, the tube composed of fine fibrous collagen was prepared having the coating layers composed of collagen on its outer and inner surfaces using the method described in Example 2. This tube was then subjected to thermal crosslinking treatment and filled with the matrix gel.

25 mm of the sciatic nerve of a cat (body weight: 5 kg) was excised, the nerve stumps on both sides were inserted into the tube prepared in the above manner and connected by ligating with 10-0 Nylon thread.

Axon transport was observed by HRP staining, and physiological function was observed by cerebrosomatic sensory induction potential and induction electromyograms immediately after or 1, 2, 3 or 4 months after surgery. The cat was sacrificed and the form of the sciatic nerve was observed both macroscopically and optical-microscopically. As a result, recovery of form and function of the sciatic nerve was observed two months after surgery.

COMPARATIVE EXAMPLE 3

With the exception of not inserting the collagen fiber bundle and not filling with the matrix gel, the polyglycolic acid mesh tube was prepared having the collagen coating layers using the method described in Example 1, after which this tube was subjected to thermal crosslinking treatment. 25 mm of the sciatic nerve of a cat (body weight: 5 kg) was excised, the nerve stumps on both sides were inserted into the tube prepared in the above manner and connected by ligating with 10-0 Nylon thread.

Axon transport was observed by HRP staining, and physiological function was observed by cerebrosomatic sensory induction potential and induction electromyograms immediately after or 1, 2, 3 or 4 months after surgery. The cat was sacrificed and the form of the sciatic nerve was observed both macroscopically and optical-microscopically.

The nerve recovered two months after surgery, while axon transport and electrophysiological function recovered three months after surgery.

COMPARATIVE EXAMPLE 4

A tube having an outer diameter of 1.0–1.5 mm was prepared from a 20 wt % aqueous gelatin solution by air-drying, and subjected to thermal dehydration crosslinking treatment at 150° C. for 24 hours.

10 mm of rat sciatic nerve was excised, the nerve stumps on both sides were inserted into the above-mentioned artificial tube for nerve and connected by ligating with 10-0 Nylon thread.

Axon transport was observed by HRP staining, and physiological function was observed by cerebrosomatic sensory induction potential and induction electromyograms immediately after or 1, 2, 3 or 4 months after surgery. The rat was sacrificed and the form of the sciatic nerve was observed both macroscopically and optical-microscopically.

A thick nerve trunk was regenerated one month after surgery, and a missing portion measuring 1.0–1.5 mm was connected. Axon transport and physiological function were both observed to recover two months after surgery.

Industrial Applicability

The artificial tube for nerve of the present invention is able to retain its shape until the nerve finishes regenerating. In addition, since it induces and promotes nerve regeneration, severed nerves regenerate faster and longer than in the case of conventional artificial tube for nerve, the state of the regenerated nerve more closely approaches the normal state, and recovery of nerve function is also favorable. In addition, it can also be used as an artificial tube for spinal cord for regeneration and recovery of damaged spinal cord.

What is claimed is:

1. An artificial tube for nerve which comprises a tube having coating layers composed of gelatin or collagen on the inner and outer surfaces of tube composed of a material being biodegradable and absorbable in vivo, and a collagen body having cavities in its lumen which pass through said tube substantially parallel to the axis of said tube; wherein, said cavities are filled with a matrix gel containing collagen, laminin, heparan sulfate proteoglycans, entactin and growth factor.

2. The artificial tube for nerve according to claim 1, wherein said tube is crosslinked, said collagen body in its lumen is in the form of a crosslinked collagen fiber bundle inserted so as to be substantially parallel to the axis of said tube, and cavities between said collagen fibers as well as cavities between said collagen fibers and said tube are filled with a matrix gel containing collagen, laminin, heparan sulfate proteoglycans, entactin and growth factor.

3. The artificial tube for nerve according to claim 1, wherein said tube is crosslinked, said collagen body in its lumen is in the form of a crosslinked collagen gel having cavities in the form of holes that pass through said tube substantially parallel to the axis of said tube, and said cavities are filled with a matrix gel containing collagen, laminin, heparan sulfate proteoglycans, entactin and growth factor.

4. The artificial tube for nerve according to claim 1, wherein said material being biodegradable and absorbable in vivo is a mesh material composed of a material selected from the group consisting of polyglycolic acid, polylactic acid, copolymer of glycolic acid and lactic acid, copolymer of lactic acid and ε-caprolactone, polydioxanone and copolymer of glycolic acid and trimethylene carbonate.

5. The artificial tube for nerve according to claim 4, wherein said material being biodegradable and absorbable in vivo in the form of a mesh material has a mesh pore size of about 10–300 µm.

6. The artificial tube for nerve according to claim 1, wherein said material being biodegradable and absorbable in vivo is composed of fine fibrous collagen, said tube coating layers are composed of collagen.

7. The artificial tube for nerve according to claim 2, wherein each of the fibers of said collagen fiber bundle is coated with a matrix gel containing collagen, laminin, heparan sulfate proteoglycans, entactin and growth factor.

8. A method for producing the artificial tube for nerve according to claim 2 including following steps: preparing a tube having coating layers composed of gelatin or collagen on the inner and outer surfaces of the tube composed of a material being biodegradable and absorbable in vivo; inserting a collagen fiber bundle substantially parallel to the axis of said tube, subjecting to crosslinking treatment, and filling a matrix gel containing collagen, laminin, heparan sulfate proteoglycans, entactin and growth factor into cavities between said collagen fibers within said tube and into cavities between said collagen fibers and said tube.

9. A process for producing the artificial tube for nerve according to claim 3 including following steps: preparing a tube having coating layers composed of gelatin or collagen on the inner and outer surfaces of the tube composed of a material being biodegradable and absorbable in vivo, inserting rod-shaped cores substantially parallel to the axis of said tube, filling said tube with a collagen solution, subjecting to crosslinking treatment, removing the cores, obtaining a tube having in its lumen a collagen gel in which cavities are formed in the form of holes that pass through said tube, and filling said cavities with a matrix gel containing collagen, laminin, heparan sulfate proteoglycans, entactin and growth factor.

* * * * *